United States Patent
Saito et al.

(10) Patent No.: US 11,406,585 B2
(45) Date of Patent: Aug. 9, 2022

(54) PHOTOCURABLE RESIN COMPOSITION FOR NAIL OR ARTIFICIAL NAIL

(71) Applicant: THREEBOND CO., LTD., Tokyo (JP)

(72) Inventors: Erika Saito, Tokyo (JP); Yugo Shirakawa, Tokyo (JP)

(73) Assignee: THREEBOND CO., LTD., Tokyo (JP)

( * ) Notice: Subject to any disclaimer, the term of this patent is extended or adjusted under 35 U.S.C. 154(b) by 483 days.

(21) Appl. No.: 16/467,155

(22) PCT Filed: Dec. 4, 2017

(86) PCT No.: PCT/JP2017/043458
§ 371 (c)(1),
(2) Date: Jun. 6, 2019

(87) PCT Pub. No.: WO2018/116798
PCT Pub. Date: Jun. 28, 2018

(65) Prior Publication Data
US 2019/0314264 A1  Oct. 17, 2019

(30) Foreign Application Priority Data
Dec. 19, 2016 (JP) .............................. JP2016-245293

(51) Int. Cl.
*A61K 8/81* (2006.01)
*A45D 29/00* (2006.01)
*A61Q 3/02* (2006.01)

(52) U.S. Cl.
CPC ............ *A61K 8/8152* (2013.01); *A45D 29/00* (2013.01); *A61Q 3/02* (2013.01)

(58) Field of Classification Search
None
See application file for complete search history.

(56) References Cited

U.S. PATENT DOCUMENTS

| | | | |
|---|---|---|---|
| 2009/0304611 A1 | 12/2009 | Tanaka et al. | |
| 2010/0074855 A1 | 3/2010 | Tanaka et al. | |
| 2016/0175212 A1* | 6/2016 | Zhou | A61K 8/8152 424/61 |
| 2016/0184199 A1 | 6/2016 | Hayakawa et al. | |
| 2018/0280258 A1* | 10/2018 | Bchir | A61K 8/19 |

FOREIGN PATENT DOCUMENTS

| | | |
|---|---|---|
| CN | 102766399 A | 11/2012 |
| JP | S55-108309 A | 8/1980 |
| JP | H10-36226 A | 2/1998 |
| JP | 2000-142788 A | 5/2000 |
| JP | 2010-013439 A | 1/2010 |
| JP | 2010-075366 A | 4/2010 |
| JP | 2016-011281 A | 1/2016 |
| JP | 2016-065000 A | 4/2016 |
| JP | 2016-121137 A | 7/2016 |
| TW | 201132362 A | 10/2011 |
| TW | 201615733 A | 5/2016 |

OTHER PUBLICATIONS

Office Action dated Jul. 12, 2021 in corresponding Japanese Application No. 2018-557645; 8 pages including English-language translation.
Taiwanese Office Action dated Sep. 14, 2021, in connection with corresponding TW Application No. 106142608 (13 pp., including machine-generated English translation).
International Search Report with an English translation and Written Opinion dated Feb. 6, 2018 in corresponding International Application No. PCT/JP2017/043458; 11 pages.
Reason for Refusal dated Dec. 27, 2021, in connection with corresponding Taiwanese Application No. 11021244140 (8 pp., including machine-generated English translation).
Office Action dated Nov. 1, 2021, in connection with corresponding Chinese Application No. 201780076894.4 (12 pp., including machine-generated English translation).

* cited by examiner

*Primary Examiner* — Nicole P Babson
(74) *Attorney, Agent, or Firm* — Maier & Maier, PLLC

(57) ABSTRACT

A photocurable resin composition for a nail or an artificial nail of the present invention includes the following components (A) to (C): component (A): a compound having a (meth)acryloyl group; component (B): a photoinitiator; and component (C): (meth)acrylic polymer particles having an average particle size of 3 to 21 μm. According to the present invention, a photocurable resin composition for a nail or an artificial nail, which has excellent transparency and workability and is capable of forming a matte coat is provided.

11 Claims, No Drawings

PHOTOCURABLE RESIN COMPOSITION FOR NAIL OR ARTIFICIAL NAIL

FIELD

The present invention relates to a photocurable resin composition appropriate for the coating of a nail.

BACKGROUND

In the field of nail care, photocurable resin compositions (UV nail gels) including photopolymerizable monomers and/or photopolymerizable oligomers have been hitherto used. These UV nail gels are used for a use application of applying makeup by decorating a nail, by applying a resin on a nail using a paintbrush or the like and irradiating the resin with light to cure. Thereby, a nail decorative film having beautiful luster and having high adhesiveness to a nail can be obtained. Furthermore, in recent years, the number of women enjoying fashion by applying nail art using UV nail gels is increasing, and as one type of nail art designs, there is a demand for a UV nail gel capable of forming a lusterless matte coat (with suppressed gloss). Further, as one of methods for realizing such a matte coat, a technique of eliminating luster by adding a filler to a photocurable resin composition and thereby generating concavities and convexities on the surface of a cured film, may be mentioned.

JP 2010-075366 A (corresponding to US 2010/074855 A) discloses an antibacterial artificial nail composition including a compound having a radical-polymerizable unsaturated double bond and an antibacterial group; an antibacterial filler and a methacrylic acid ester-based polymer as fillers; a compound having a radical-polymerizable unsaturated double bond; and a polymerization initiator material.

SUMMARY

However, when the antibacterial artificial nail composition disclosed in the above-mentioned document is used, the cured product thus obtainable has luster, and a matte coat cannot be provided. Furthermore, when a filler or the like is mixed into the resin composition in order to form a matte coat, there is a problem that the resin composition may become white and cloudy, and viscosity may increase which deteriorates workability, or the like. Thus, it has been difficult to realize a UV nail gel capable of forming a matte coat.

The present invention has been achieved under such circumstances, and it is an object of the invention to provide a photocurable resin composition for a nail or an artificial nail, which has excellent transparency and workability and is capable of forming a matte coat.

The inventors of the present invention conducted a thorough study in order to solve the problems described above. As the result, the inventors found that the above-described problem can be solved by a photocurable resin composition for a nail or an artificial nail, which includes particular components (A) to (C) that will be described below, and thus the inventors completed the present invention. That is, the various objects described above can be achieved by the following embodiments.

The gist of the present invention will be described below.

A first embodiment of the present invention is a photocurable resin composition for a nail or an artificial nail, including the following components (A) to (C):

component (A): a compound having a (meth)acryloyl group);

component (B): a photoinitiator; and component (C): (meth)acrylic polymer particles having an average particle size of 3 to 21 µm.

A second embodiment of the present invention is the photocurable resin composition for a nail or an artificial nail according to the first embodiment, in which the average particle size of the (meth)acrylic polymer particles of the component (C) is 5 to 14 µm.

A third embodiment of the present invention is a photocurable resin composition for a nail or an artificial nail according to any one of the first embodiment or the second embodiment, in which the component (A) includes a (meth)acrylate oligomer and/or a (meth)acrylate monomer.

A fourth embodiment of the present invention is a photocurable resin composition for a nail or an artificial nail according to any one of the first embodiment to the third embodiment, in which the component (A) includes a urethane (meth)acrylate oligomer.

A fifth embodiment of the present invention is a photocurable resin composition for a nail or an artificial nail according to any one of the first embodiment to the fourth embodiment, in which the component (C) is contained in an amount of 45 to 155 parts by mass with respect to 100 parts by mass of the component (A).

A sixth embodiment of the present invention is a photocurable resin composition for a nail or an artificial nail according to anyone of the first embodiment to the fifth embodiment, in which the component (C) is polymethylmethacrylate particles.

A seventh embodiment of the present invention is a cured product of the photocurable resin composition for a nail or an artificial nail set forth in any one of the first embodiment to the sixth embodiment.

An eighth embodiment of the present invention is a method for coating a nail or an artificial nail, including applying the photocurable resin composition for a nail or an artificial nail set forth in anyone of the first embodiment to the seventh embodiment on a nail or an artificial nail to form a coating film, and then irradiating the coating film with energy rays to cure the coating film.

DETAILED DESCRIPTION

Embodiments of the present invention will be described below. The photocurable resin composition for a nail or an artificial nail (hereinafter, also simply referred to as "photocurable resin composition") related to an embodiment of the present invention includes the following components (A) to (C):

component (A): a compound having a (meth)acryloyl group;

component (B): a photoinitiator; and component (C): (meth)acrylic polymer particles having an average particle size of 3 to 21 µm.

Since the photocurable resin composition having the above-described configuration has satisfactory transparency and also has relatively low viscosity, the photocurable resin composition also has excellent workability. Furthermore, a cured product formed by curing this photocurable resin composition has matte characteristics (low glossiness).

The details of this mechanism are not clearly known; however, it is speculated that the type of the material ((meth)acrylic polymer) and the average particle size (average particle size 3 to 21 µm) of the particles that are included as component (C) affect transparency and workability (viscosity) of the photocurable resin composition and the matte characteristics (low glossiness) of the cured product. Particularly, when the average particle size of the particles to be included as component (C) is less than 3 μm, glossiness of the cured product is increased, and sufficient matte characteristics are not obtained (a delustering effect is not obtained). Furthermore, when the average particle size is more than 21 μm, a uniform matte coat cannot be formed. In contrast, when the average particle size of the particles to be included as component (C) is 3 to 21 μm, a uniform matte coat having excellent matte characteristics (low glossiness) can be formed. Furthermore, by setting the material type of component (C) to a (meth)acrylic polymer, a photocurable resin composition having a viscosity appropriate for applying (excellent workability) in addition to excellent transparency can be obtained.

Therefore, according to the present invention, a photocurable resin composition that has excellent transparency and workability and is capable of forming a matte coat is provided. Furthermore, according to the present invention, even in a case of curing with a light source having a long wavelength such as 400 nm, effects similar to those described above can be obtained. Therefore, the photocurable resin composition according to the present invention is suitably used also for the use of a UV nail gel that is capable of forming a matte coat. Meanwhile, the above-described mechanism is based on speculations, and the right or wrong of this mechanism shall not affect the technical scope of the present invention.

Hereinafter, the photocurable resin composition according to the present invention will be explained in detail. Meanwhile, in the present specification, the expression "X to Y" is used to mean to include the values described before and after (X and Y) as the lower limit and the upper limit, and means "more than or equal to X and less than or equal to Y". Furthermore, unless particularly stated otherwise, the operation and measurement of physical properties and the like are carried out under the conditions of room temperature (20° C. to 25° C.)/relative humidity of 40% to 50% RH.

[Photocurable Resin Composition for Nail or Artificial Nail]

<Component (A)>

Component (A) that is included in the photocurable resin composition according to the present invention is a compound having a (meth)acryloyl group. Meanwhile, the compound having a (meth)acryloyl group may have the (meth) acryloyl group in the form of a (meth)acryloyloxy group. In the present specification, the term "(meth)acryloyl" includes both acryloyl and methacryloyl. Therefore, for example, the term "(meth)acryloyl group" includes both an acryloyl group ($H_2C=CH-C(=O)-$) and a methacryloyl group ($H_2C=C(CH_3)-C(=O)-$). Furthermore, similarly, the term "(meth)acryl" includes both acryl and methacryl. Therefore, for example, the term "(meth)acrylic acid" includes both acrylic acid and methacrylic acid.

Component (A) is not particularly limited as long as it is a compound having one or more (meth)acryloyl groups, and may have another functional group such as a carboxy group, a phosphoric acid group, a hydroxyl group, or the like.

The compound having a (meth)acryloyl group as component (A) is preferably an oligomer or a monomer, each having one or more (meth)acryloyl groups, from the viewpoint of obtaining satisfactory curing rate and workability (adequate fluidity at the time of application). In the present specification, an "oligomer" refers to a polymer in which monomer units (including monomer units other than a (meth)acrylate monomer) are repeated about two to several ten times. Preferably, the "oligomer" has the weight average molecular weight of more than or equal to 1,000 and less than or equal to 100,000.

The weight average molecular weight of the oligomer as component (A) is preferably 1,000 to 100,000, more preferably 2,000 to 30,000, and particularly preferably 3,000 to 20,000. With such a range, durability of a cured product can be made satisfactory while low viscosity is maintained. Meanwhile, in the present specification, as the weight average molecular weight, a value measured by Gel Permeation Chromatography (GPC) using polystyrenes as standard substances is employed.

It is preferable that component (A) is a liquid (liquid form) (that is, has fluidity) in an atmosphere at 25° C. Specifically, in order to improve the workability at the time of application, the viscosity at 25° C. measured using an EHD type rotary viscometer is preferably 50 Pa·s or less, and more preferably 40 Pa·s or less (lower limit: 1 mPa·s).

Furthermore, regarding component (A), a compound having satisfactory compatibility with component (B) that will be described below in detail is preferably used.

From the viewpoint of obtaining a satisfactory curing rate and high transparency, as component (A) according to the present invention, it is preferable to use a compound such as a (meth)acrylate oligomer, a (meth)acrylate monomer, or the like. That is, it is preferable that component (A) includes a (meth)acrylate oligomer and/or a (meth)acrylate monomer. Furthermore, it is preferable that component (A) is a (meth) acrylate oligomer and/or a (meth)acrylate monomer.

Hereinafter, a (meth)acrylate oligomer and a (meth)acrylate monomer, which are preferably used as component (A), will be explained. When a (meth)acrylate oligomer is added, effects of enhancing the adhesiveness to a nail or an artificial nail and enhancing the curability and strength of the photocurable resin composition (coating film) are obtained. On the other hand, when a (meth)acrylate monomer is added, the viscosity of the photocurable resin composition can be decreased. Therefore, in order to obtain these advantages, it is preferable that component (A) includes both a (meth) acrylate oligomer and a (meth)acrylate monomer.

((Meth)acrylate Oligomer)

The (meth)acrylate oligomer is not particularly limited as long as it is an oligomer having one or more (meth)acryloyl groups. The number of (meth)acryloyl groups included in one molecule is not particularly limited; however, for the purpose of obtaining a cured product having satisfactory hardness, the number is preferably 1 to 10, and more preferably 2 to 8.

The weight average molecular weight of the (meth) acrylate oligomer is preferably 1,000 to 100,000, more preferably 2,000 to 30,000, and particularly preferably 3,000 to 20,000. With such a range, durability of a cured product can be made satisfactory while low viscosity is maintained.

Specific examples of the (meth)acrylate oligomer are not particularly limited, but include an ester (meth)acrylate oligomer having an ester bond in the molecule ((meth) acrylate oligomer having an ester bond in the main skeleton), an ether (meth)acrylate oligomer having an ether group ((meth)acrylate oligomer having an ether bond in the main skeleton), a urethane (meth)acrylate oligomer having a urethane bond ((meth)acrylate oligomer having a urethane bond in the main skeleton), and the like. For the (meth) acrylate oligomer described above, any of a commercially available product or a synthetic product may be used. Furthermore, regarding the (meth)acrylate oligomer, one kind may be used alone, or two or more kinds may be used in combination. Furthermore, an oligomer other than that can also be used in combination.

Particularly, from the viewpoints of adhesiveness to a nail and durability of the photocurable resin composition and a cured product thereof, it is preferable that component (A) includes a urethane (meth)acrylate oligomer. Furthermore, from a similar viewpoint, it is more preferable that the (meth)acrylate oligomer as component (A) is a urethane (meth)acrylate oligomer.

An ester (meth)acrylate oligomer having an ester bond can be synthesized by forming an ester bond by a reaction between a polyol and a polyvalent carboxylic acid, and then adding a compound having a hydroxyl group and a (meth) acryloyl group in the molecule or (meth)acrylic acid to an unreacted hydroxyl group of the ester compound thus obtained; however, the method for synthesizing this (meth) acrylate oligomer is not limited to this method. Specific examples of a commercially available product include ARONIX (registered trademark) M-6100, M-6200, M-6250, M-6500, M-7100, M-7300K, M-8030, M-8060, M-8100, M-8530, M-8560, and M-9050 (manufactured by Toagosei Co., Ltd.); UV-3500BA, UV3520TL, UV-3200B, and UV-3000B (manufactured by Nippon Synthetic Chemical Industry Co., Ltd.), and the like; however, examples are not limited to these.

An ether (meth)acrylate oligomer having an ether bond can be synthesized by adding a compound having a hydroxyl group and a (meth)acryloyl group in the molecule or (meth) acrylic acid to a hydroxyl group of an aliphatic polyether polyol, or a hydroxyl group of an aromatic polyether polyol such as bisphenol or the like; however, the method for synthesizing this (meth)acrylate oligomer is not limited to this method. Specific examples of a commercially available product include UV-6640B, UV-6100B, and UV-3700B (manufactured by Nippon Synthetic Chemical Industry Co., Ltd.); LIGHT ACRYLATE (registered trademark) 3EG-A, 4EG-A, 9EG-A, 14EG-A, PTMGA-250, BP-4EA, BP-4PA, and BP-10EA, LIGHT ESTER 4EG, 9EG, and 14EG (manufactured by Kyoeisha Chemical Co., Ltd.); EBE-CRYL (registered trademark) 3700 (manufactured by Daicel-Cytec Co., Ltd.; and the like; however, the examples are limited to these.

A urethane (meth)acrylate oligomer having a urethane bond can be synthesized by forming a urethane bond by a reaction between a polyol and a polyisocyanate, and adding a compound having a hydroxyl group and a (meth)acryloyl group in the molecule or (meth)acrylic acid to an unreacted isocyanate group; however, the method for synthesizing this (meth)acrylate oligomer is not limited to this method. Specific examples of a commercially available product include AH-600, AT-600, UA-306H, and UF-8001G (manufactured by Kyoeisha Chemical Co., Ltd.); RUA-071, RUA-003VE, RUA-075, and RUA-048 (manufactured by Asia Industry Co., Ltd.); and the like; however, the examples are not limited to these.

Furthermore, regarding the (meth)acrylate oligomer as the component (A), one kind may be used alone, or two or more kinds may be used in combination.

((Meth)acrylate Monomer)

The (meth)acrylate monomer is not particularly limited as long as it is a monomer having one or more (meth)acryloyl groups. The number of (meth)acryloyl groups included in one molecule is not particularly limited; however, for the purpose of obtaining a cured product having satisfactory hardness, the number is preferably 1 to 5, more preferably 1 to 3, and particularly preferably 1.

In order to lower the viscosity of the photocurable resin composition and to enhance workability at the time of application, the molecular weight of the (meth)acrylate monomer is preferably less than 1,000, and more preferably 500 or less. The molecular weight can be measured by a known method such as a gas chromatography-mass analysis (GC-MS) method or the like. Furthermore, the molecular weight can also be specified by specifying the structure by a method such as NMR or the like, and performing calculation based on the structure.

Specific examples of the (meth)acrylate monomer are not particularly limited; however, a (meth)acrylic acid ester monomer, a (meth)acrylamide monomer, and the like, all of which are monofunctional, bifunctional, or trifunctional (having one to three (meth)acryloyl groups) may be mentioned. For the (meth)acrylate monomer, any of a commercially available product or a synthetic product may be used. Furthermore, regarding the (meth)acrylate monomer, one kind may be used alone, or two or more kinds may be used in combination. Furthermore, other monomers can also be used in combination.

Specific examples of a monofunctional (meth)acrylic acid ester monomer include lauryl (meth)acrylate, stearyl (meth) acrylate, ethyl carbitol (meth)acrylate, tetrahydrofurfuryl (meth)acrylate, caprolacton-modified tetrahydrofurfuryl (meth)acrylate, cyclohexyl (meth)acrylate, dicyclopentanyl (meth)acrylate, isobornyl (meth)acrylate, benzyl (meth) acrylate, phenyl (meth)acrylate, phenoxyethyl (meth)acrylate, phenoxydiethylene glycol (meth)acrylate, phenoxytetraethylene glycol (meth)acrylate, nonyl phenoxyethyl (meth)acrylate, nonyl phenoxytetraethylene glycol (meth) acrylate, methoxy diethylene glycol (meth)acrylate, ethoxy diethylene glycol (meth)acrylate, butoxyethyl (meth)acrylate, butoxytriethylene glycol (meth)acrylate, 4-hydroxybutyl (meth)acrylate, methoxydipropylene glycol (meth) acrylate, 2-hydroxyethyl (meth)acrylate, 2-hydroxypropyl (meth)acrylate, glycerol (meth)acrylate, epichlorohydrin-modified butyl (meth)acrylate, epichlorohydrin-modified phenoxy (meth)acrylate, N,N-dimethylaminoethyl (meth) acrylate, N,N-diethylaminoethyl (meth)acrylate, and the like; however, the examples are not limited to these.

Examples of the monofunctional (meth)acrylic acid ester monomer also include a (meth)acrylic acid ester monomer having an acidic group. Particularly, a carboxylic acid or a phosphoric acid respectively having a (meth)acryloyl group in the molecule, or the like is referred to. Examples of a carboxylic acid having a (meth)acryloyl group in the molecule include (meth)acrylic acid, 3-(meth)acryloyloxypropylsuccinic acid, 4-(meth)acryloyloxybutylsuccinic acid, 2-(meth)acryloyloxyethylmaleic acid, 3-(meth)acryloyloxypropylmaleic acid, 4-(meth)acryloyloxybutylmaleic acid, 2-(meth)acryloyloxyethylhexahydrophthalic acid, 3-(meth) acryloyloxypropylhexahydrophthalic acid, 4-(meth)acryloyloxybutylhexahydrophthalic acid, 2-(meth)acryloyloxyethylphthalic acid, 3-(meth)acryloyloxypropylphthalic acid, 4-(meth)acryloyloxybutylphthalic acid, and the like. Examples of a phosphoric acid having a (meth)acryloyl group in the molecule include 2-hydroxyethyl methacrylate acid phosphate, and the like. However, the examples are not limited to these.

Specific examples of a bifunctional (meth)acrylic acid ester monomer include 1,3-butylene glycol di(meth)acrylate, 1,4-butylene glycol di(meth)acrylate, tricyclodecane dimethanol di(meth)acrylate, neopentyl glycol di(meth) acrylate, 1,6-hexane glycol di(meth)acrylate, ethylene glycol diacrylate, tetraethylene glycol di(meth)acrylate, polyethylene glycol di(meth)acrylate, propylene glycol di(meth)

acrylate, tripropylene glycol di(meth)acrylate, ethylene oxide-modified neopentyl glycol di(meth)acrylate, propylene oxide-modified neopentyl glycol di(meth)acrylate, bisphenol A di(meth)acrylate, ethylene oxide-modified bisphenol A di(meth)acrylate, epichlorohydrin-modified bisphenol A di(meth)acrylate, ethylene oxide-modified bisphenol S di(meth)acrylate, neopentyl glycol-modified trimethylolpropane di(meth)acrylate, dicyclopentenyl di(meth)acrylate, ethylene oxide-modified dicyclopentenyl di(meth)acrylate, di(meth)acryloyl isocyanurate, and the like; however, the examples are not limited to these.

Specific examples of a trifunctional (meth)acrylic acid ester monomer include trimethylolpropane tri(meth)acrylate, trimethylolpropane tri(meth)acrylate, pentaerythritol tri(meth)acrylate, ethylene oxide (EO)-modified trimethylolpropane tri(meth)acrylate, propylene oxide (PO)-modified trimethylolpropane tri(meth)acrylate, epichlorohydrin (ECH)-modified trimethylolpropane tri(meth)acrylate, ECH-modified glycerol tri(meth)acrylate, tris((meth)acryloyloxyethyl) isocyanurate, and the like; however, the examples are not limited to these.

Specific examples of a (meth)acrylamide monomer include dimethyl (meth)acrylamide, (meth)acryloylmorpholine, diethyl (meth)acrylamide, and the like; however, the examples are not limited to these.

It is preferable that the (meth)acrylate monomer has an alicyclic structure. In the present specification, the phrase "has an alicyclic structure" means that the monomer has a cyclic structure of a hydrocarbon. Examples of the alicyclic structure include a monocyclic cycloalkyl group such as a cyclopropyl group, a cyclobutyl group, a cyclopentyl group, a cyclohexyl group, a methylcyclohexyl group, a dimethylcyclohexyl group, or the like; a monocyclic cycloalkenyl group such as a cyclobutenyl group, a cyclopentenyl group, a cyclohexenyl group, or the like; a polycyclic cycloalkyl group such as a hydronaphthyl group, a 1-adamantyl group, a 2-adamantyl group, a norbornyl group, a methylnorbornyl group, an isobornyl group, a dicyclopentanyl group, a tricyclodecyl group, tetracyclododecyl group, or the like; a polycyclic cycloalkenyl group such as a dicyclopentenyl group, a dicyclopentenyloxyethyl group, or the like; and the like. However, the examples are not limited to these.

Regarding the alicyclic structure, one kind may be included alone in one molecule, or two or more kinds may be included. Among those described above, from the viewpoint of making it easy to obtain the effects of the present invention, it is preferable that a (meth)acrylate monomer as component (A) includes a polycyclic cycloalkyl group as an alicyclic structure. That is, it is preferable that a (meth)acrylate monomer as component (A) includes a (meth)acrylate monomer having a polycyclic cycloalkyl group.

Examples of such a (meth)acrylate monomer including a polycyclic cycloalkyl group include dicyclopentanyl (meth)acrylate, isobornyl (meth)acrylate, and the like. Among them, in order to obtain a cured product having excellent hardness, it is preferable that component (A) includes isobornyl (meth)acrylate.

From the viewpoint of enhancing adhesiveness to a nail or an artificial nail and durability and also obtaining a sufficient curing rate, and from the viewpoint of securing satisfactory workability, it is preferable that both a (meth)acrylate oligomer and a (meth)acrylate monomer are included in component (A). That is, it is preferable that component (A) includes a (meth)acrylate oligomer and a (meth)acrylate monomer. As such, in a case in which both the oligomer and the monomer are included, the ratio (mass ratio) of the oligomer and the monomer is not particularly limited; however, it is preferable that the ratio (mass ratio) of oligomer:monomer is 50:50 to 95:5, and more preferably 55:45 to 80:20. As a (meth)acrylate oligomer is included, the adhesiveness to a nail or an artificial nail and durability of the photocurable resin composition and a cured product thereof are enhanced. Furthermore, such effects become more noticeable as the oligomer is included at a mass ratio that is equal to or more than the mass ratio of a (meth)acrylate monomer.

Furthermore, it is preferable that component (A) includes a urethane (meth)acrylate oligomer having a urethane bond and a (meth)acrylate monomer; it is more preferable that component (A) includes a urethane (meth)acrylate oligomer having a urethane bond and a monofunctional (meth)acrylic acid ester monomer; and it is particularly preferable that component (A) includes a urethane (meth)acrylate oligomer having a urethane bond and a monofunctional (meth)acrylic acid ester monomer having an alicyclic structure. At this time, the ratio (mass ratio) between a urethane (meth)acrylate oligomer having a urethane bond and the respective (meth)acrylate monomers is also not particularly limited; however, it is preferable when the ratio is within a range similar to that of the "ratio of oligomer:monomer".

<Component (B)>

Component (B) that is included in the photocurable resin composition according to the present invention is a photoinitiator (photopolymerization initiator). Examples of a photoinitiator include a radical-based photoinitiator that generates a radical species by irradiation with energy rays such as visible light rays, ultraviolet rays, X-rays, an electron beam or the like; a cationic photoinitiator that generates a cation species; an anionic photogenerating agent that generates an anion species; and the like. However, among them, a radical-based photoinitiator is preferred.

Specific examples of the radical-based photoinitiator of component (B) include acetophenones such as diethoxyacetophenone, 2-hydroxy-2-methyl-1-phenylpropan-1-one, benzyl dimethyl ketal, 4-(2-hydroxyethoxy)phenyl-(2-hydroxy-2-propyl) ketone, 1-hydroxycyclohexyl phenyl ketone, 2-methyl-2-morpholino(4-thiomethylphenyl)propan-1-one, 2-benzyl-2-dimethylamino-1-(4-morpholinophenyl)butanone, 2-hydroxy-2-methyl-1-[4-(1-methylvinyl)phenyl]propanone oligomer, and the like; benzoins such as benzoin, benzoin methyl ether, benzoin ethyl ether, benzoin isopropyl ether, benzoin isobutyl ether, and the like; benzophenones such as benzophenone, methyl o-benzoylbenzoate, 4-phenylbenzophenone, 4-benzoyl-4'-methyl-diphenylsulfide, 3,3',4,4'-tetra(t-butylperoxycarbonyl)benzophenone, 2,4,6-trimethylbenzophenone, 4-benzoyl-N,N-dimethyl-N-[2-(1-oxo-2-propenyloxy)ethyl]benzenemethanaminium bromide, (4-benzoylbenzyl)trimethylammonium chloride, and the like; thioxanthones such as 2-isopropylthioxanthone, 4-isopropylthioxanthone, 2,4-diethylthioxanthone, 2,4-dichlorothioxanthone, 1-chloro-4-propoxythioxanthone, 2-(3-dimethylamino-2-hydroxy)-3,4-dimethyl-9H-thioxanthon-9-one mesochloride, and the like; acylphosphine oxides such as 2,4,6-trimethylbenzoyl-diphenyl-phosphine oxide, bis(2,4,6-trimethylbenzoyl)-phenylphosphine oxide, and the like; and the like. However, the examples are not limited to these. Among these, it is preferable that component (B) includes at least one selected from acetophenones and acylphosphine oxides. Furthermore, these may be used singly, or a plurality of components (B) can also be used in combination.

The content of component (B) (in a case in which two or more kinds are included, the sum total amount thereof) in the photocurable resin composition according to the present invention is such that with respect to 100 parts by mass of component (A), component (B) is preferably 2 to 25 parts by mass, more preferably 4 to 15 parts by mass, and particularly preferably more than or equal to 8 parts by mass and less than 15 parts by mass. In a case in which component (B) is 2 parts by mass or more, furthermore 4 parts by mass or more, or 8 parts by mass or more, with respect to 100 parts by mass of component (A), photocurability can be maintained more satisfactorily. On the other hand, in a case in which component (B) is 25 parts by mass or less, furthermore, 15 parts by mass or less, or less than 15 parts by mass, with respect to 100 parts by mass of component (A), thickening does not occur during storage, and storage stability can be further improved.

From the viewpoint of further enhancing photocurability and further suppressing coloration, it is preferable that component (B) includes a visible light type photoinitiator, and it is more preferable when component (B) includes both a visible light type photoinitiator and a photoinitiator other than the photoinitiator (non-visible light type photoinitiator). In the case of using a visible light type photoinitiator and a non-visible light type photoinitiator, it is preferable that the visible light type photoinitiator is included in an amount of 70% by mass or less with respect to the total amount of component (B) (lower limit: more than 0% by mass). By adjusting the amount to be in the above-described range, yellowing of the cured product can be further suppressed. From a similar viewpoint, it is more preferable that the visible light type photoinitiator is included in an amount of 60% by mass or less with respect to the total amount of component (B). On the other hand, it is preferable that a visible light type photoinitiator is included in an amount of 50% by mass or more with respect to the total amount of component (B). By adjusting the amount to be in the above-described range, photocurability of the photocurable resin composition is further enhanced.

Here, a visible light type photoinitiator is a photoinitiator having an absorption maximum in the visible light region (wavelength 400 to 800 nm, preferably wavelength in the range of 400 to 500 nm), and any known agent can be used. However, an acylphosphine oxide-based photopolymerization initiator mainly containing a phosphorus atom may be mentioned. Specific examples include 2,4,6-trimethylbenzoyl diphenylphosphine oxide, bis(2,4,6-trimethylbenzoyl) phenylphosphine oxide, and the like; however, the examples are not limited to these. Furthermore, a non-visible light type photoinitiator is a photoinitiator other than the visible light type photoinitiator, and any known ultraviolet light type photoinitiator or the like can be used.

<Component (C)>

Component (C) included in the photocurable resin composition according to the present invention is (meth)acrylic polymer particles having an average particle size of 3 to 21 µm. Component (C) is a component that can function as a filler and contributes to the matte characteristics (low glossiness) of the photocurable resin composition.

As the average particle size of the (meth)acrylic polymer particles as component (C) is in the range of 3 to 21 µm, a sufficient delustering effect is obtained, and also, workability at the time of application is enhanced. Therefore, a uniform matte coat can be formed. Particularly, by adjusting the average particle size to be 3 µm or more, a matte coat in which gloss has been sufficiently suppressed can be formed. Furthermore, by adjusting the average particle size to be 21 µm or less, viscosity of the photocurable resin composition is decreased, and particularly workability at the time of performing application becomes satisfactory. As the result, a uniform matte coat can be formed.

Meanwhile, in the present specification, the "average particle size" refers to a value of the cumulative volume 50% particle size that can be determined by measuring a particle size distribution with a laser diffraction type particle size distribution analyzer.

From the viewpoint of obtaining sufficient matte characteristics (delustering effect), enhancing workability at the time of application, and forming a uniform matte coat, the average particle size of the (meth)acrylic polymer particles as component (C) is preferably 4 µm to 15 µm, more preferably more than 4 µm and less than 15 µm, particularly preferably 5 to 14 µm, and most preferably 6 to 10 µm.

Component (C) is preferably solid at room temperature (25° C.), and the shape is preferably a spherical shape. Here, the "spherical shape" is not necessarily needed to be a complete sphere, and includes all whose basic shape is a sphere.

The (meth)acrylic polymer particles as component (C) may be particles containing a (meth)acrylic polymer and may contain another polymer; however, from the viewpoint of obtaining high transparency, it is preferable that the (meth)acrylic polymer particles as component (C) do not contain a polymer other than a (meth)acrylic polymer. That is, it is preferable that the (meth)acrylic polymer particles are substantially composed of a (meth)acrylic polymer only.

The weight average molecular weight of the (meth)acrylic polymer is preferably more than 100,000 and less than or equal to 11,000,000. With such a range, satisfactory dispersibility to component (A) is exhibited, and while the viscosity of the photocurable resin composition is reduced, durability of the cured product can be made satisfactory.

The (meth)acrylic polymer that constitutes the (meth)acrylic polymer particles may be any polymer that uses a (meth)acrylic acid ester as a raw material. Examples of such a polymer include a polymer of a (meth)acrylic acid ester, a copolymer of a (meth)acrylic acid ester and another radical-polymerizable monomer, and the like.

Specific examples of the (meth)acrylic acid ester include benzyl (meth)acrylate, 4-biphenyl (meth)acrylate, butyl (meth)acrylate, sec-butyl (meth)acrylate, t-butyl (meth)acrylate, 4-t-butylphenyl (meth)acrylate, 4-chlorophenyl (meth)acrylate, pentachlorophenyl (meth)acrylate, 4-cyanobenzyl (meth)acrylate, cyanomethyl (meth)acrylate, cyclohexyl (meth)acrylate, 2-ethoxyethyl (meth)acrylate, ethyl (meth)acrylate, 2-ethylhexyl (meth)acrylate, heptyl (meth)acrylate, hexyl (meth)acrylate, isobornyl (meth)acrylate, isopropyl (meth)acrylate, methyl (meth)acrylate, 3,5-dimethyladamantyl (meth)acrylate, 2-naphthyl (meth)acrylate, neopentyl (meth)acrylate, octyl (meth)acrylate, phenethyl (meth)acrylate, phenyl (meth)acrylate, propyl (meth)acrylate, tolyl (meth)acrylate, amyl (meth)acrylate, tetrahydrofurfuryl (meth)acrylate, 2-hydroxyethyl acrylate, 3-hydroxypropyl acrylate, 2-hydroxypropyl acrylate, 4-hydroxybutyl (meth)acrylate, 5-hydroxypentyl (meth)acrylate, allyl (meth)acrylate, 2-allyloxyethyl (meth)acrylate, propargyl (meth)acrylate, and the like; however, the examples are not limited to these. These may be used singly, or two or more kinds may be used in combination. Particularly, from the viewpoint of transparency, the polymer that constitutes the (meth)acrylic polymer particles of component (C) is preferably a polymer of a methacrylic acid ester, more preferably a polymer of methyl (meth)acrylate, and particularly preferably a polymer of methylmethacrylate.

That is, component (C) is preferably polymethyl (meth) acrylate particles, and more preferably polymethylmethacrylate particles.

Examples of the other radical-polymerizable monomer include (meth)acrylamides, styrenes, (meth)acrylonitriles, vinyl ethers, and the like.

Regarding the (meth)acrylic polymer (particles), any of a commercially available product or a synthetic product may be used. (Meth)acrylic polymer (particles) can be obtained by (co)polymerizing a (meth)acrylic acid ester and another radical-polymerizable monomer that is used as necessary, by a known method such as suspension polymerization or the like. Specific examples of a commercially available product include ART PEARL (registered trademark) GR-400, GR-600, GR-800, J-6PF, J-7PY, J-7P, SE-006T, SE-010T, SE-020T, G-400, and G-800 (manufactured by Negami Chemical Industrial Co., Ltd.); GANZ PEARL (registered trademark) GM-0600 and GMP-0820 (manufactured by Aika Kogyo Co., Ltd.); and the like. However, the examples are not limited to these.

The content of component (C) (in a case in which two or more kinds are included, the sum total amount) in the photocurable resin composition according to the present invention is such that component (C) is contained in an amount of preferably 45 to 155 parts by mass, more preferably 55 to 150 parts by mass, and particularly preferably 100 to 130 parts by mass, with respect to 100 parts by mass of component (A). In a case in which component (C) is 45 parts by mass or more, furthermore 55 parts by mass or more, or 100 parts by mass or more, with respect to 100 parts by mass of component (A), a matte coat having sufficient matte characteristics (low glossiness) can be formed. On the other hand, in a case in which component (C) is 155 parts by mass or less, furthermore 150 parts by mass or less, or 130 parts by mass or less, with respect to 100 parts by mass of component (A), the viscosity of the photocurable resin composition is decreased, and workability particularly at the time of performing application becomes satisfactory.

<Optional Components>

According to the present invention, to the extent that does not impair the purpose of the present invention, additives such as a filler, an electrically conductive filler, a silane coupling agent, a plasticizer, a defoaming agent, a pigment, an antirust agent, a leveling agent, a dispersant, a rheology adjusting agent, a flame retardant, and the like can be used in addition to the components (A) to (C).

(Filler)

The photocurable resin composition according to the present invention may further include a filler to the extent that does not impair storage stability, for the purpose of ameliorating the elastic modulus of the cured product, fluidity, and the like. Specific examples of such a filler include an inorganic powder (inorganic filler), an organic powder (organic filler) other than component (C), and the like.

Examples of a filler of an inorganic powder (inorganic filler) include glass, fumed silica, alumina, mica, ceramics, a silicone rubber powder, calcium carbonate, aluminum nitride, a carbon powder, kaolin clay, dried clay mineral, dry diatomaceous earth, kaolin, and the like; however, the examples are not limited to these. These may be used respectively singly, or mixtures of two or more kinds may also be used. The content of the inorganic powder (inorganic filler) (in a case in which two or more kinds are included, the sum total amount) is preferably about 0.1 to 200 parts by mass with respect to 100 parts by mass of component (A).

Among them, fumed silica can be incorporated for the purpose of adjusting the viscosity of the photocurable resin composition or increasing the mechanical strength of the cured product. Preferably, fumed silica or the like that has been surface-treated with dimethylsilane, trimethylsilane, alkylsilane, methacryloxysilane, organochlorosilane, polydimethylsiloxane, hexamethyldisilazane, or the like, is used. Examples of a commercially available product of fumed silica include AEROSIL (registered trademark) R972, R972V, R972CF, R974, R976, R976S, R9200, RX50, NAX50, NX90, RX200, RX300, R812, R812S, R8200, RY50, NY50, RY200S, RY200, RY300, R104, R106, R202, R805, R816, T805, R711, R7200, and the like (manufactured by Nippon Aerosil Co., Ltd.); however, the examples are not limited to these. These may be used respectively singly, or mixtures of two or more kinds may also be used.

Examples of a filler of an organic powder (organic filler) other than component (C) include polyethylene, polypropylene, polystyrene, nylon, polyester, polyvinyl alcohol, polyvinyl butyral, and polycarbonate; however, the examples are not limited to these. These may be used respectively singly, or mixtures of two or more kinds may also be used. The content of the organic powder (organic filler) (in a case in which two or more kinds are included, the sum total amount) is preferably about 0.1 to 200 parts by mass with respect to 100 parts by mass of component (A).

The photocurable resin composition according to the present invention may further include an electrically conductive filler. Examples include gold, silver, platinum, nickel, palladium, and plated particles obtained by coating organic polymer particles with metal thin films; however, the examples are not limited to these. These may be used respectively singly, or mixtures of two or more kinds may also be used.

(Silane Coupling Agent)

According to the present invention, a silane coupling agent may also be added. Examples of the silane coupling agent include γ-chloropropyltrimethoxysilane, octenyltrimethoxysilane, glycidoxyoctyltrimethoxysilane, β-(3,4-epoxycyclohexyl)ethyltrimethoxysilane, γ-glycidoxypropyltrimethoxysilane, γ-mercaptopropyltrimethoxysilane, γ-aminopropyltriethoxysilane, N-β-(aminoethyl)-γ-aminopropyltrimethoxysilane, N-β-(aminoethyl)-γ-aminopropylmethyldimethoxysilane, γ-ureidopropyltriethoxysilane, p-styryltrimethoxysilane, and the like; however, the examples are not limited to these. These may be used respectively singly, or mixtures of two or more kinds may also be used. The content of a tackifier is preferably 0.05 to 30 parts by mass, and more preferably 0.2 to 10 parts by mass, with respect to 100 parts by mass of component (A).

[Method for Producing Photocurable Resin Composition for Nail or Artificial Nail]

The method for producing the photocurable resin composition of the present invention is not particularly limited, and production can be carried out by any conventionally known method. For example, for component (A) to component (C) and components that are optionally added (optional components), predetermined amounts are respectively weighed, the components are added sequentially, irrespective of the order, or simultaneously to a mixing pot, and then the components are mixed using a mixing means such as a planetary mixer or the like. Thereby, the photocurable resin composition of the present invention can be obtained. At this time, the production conditions are not particularly limited; however, for the purpose of suppressing the viscosity from increasing, it is preferable that the production is carried out under light-shielded conditions. Furthermore, from the viewpoint of suppressing polymerization of component (A) in particular, and maintaining the viscosity of the photocurable resin composition thus obtainable low, it is preferable that the mixing temperature is set to a temperature of 10° C. to 50° C., and it is preferable that the mixing time is 0.1 to 5 hours.

[Use Application of Photocurable Resin Composition for Nail or Artificial Nail]

The photocurable resin composition according to the present invention also has excellent transparency and workability. Furthermore, when this composition is used, a uniform matte coat can be formed. Therefore, the photocurable resin composition according to the present invention is useful when a nail or an artificial nail is subjected to nail color art of a texture with suppressed gloss. Therefore, the photocurable resin composition according to the present invention is preferably a photocurable composition for nail or artificial nail coating. Therefore, when an operation of applying using a brush, a paintbrush, or the like, from the viewpoint of improving workability, the viscosity of the photocurable resin composition at 25° C. is preferably 100 Pa·s or less, more preferably 50 Pa·s or less, even more preferably less than 50 Pa·s, particularly preferably 45 Pa·s or less, and most preferably 30 Pa·s or less. On the other hand, the lower limit of the viscosity is not particularly limited; however, from the viewpoint of making it easier to carry out curing after application, the viscosity is preferably 3 Pa·s or more. Regarding the viscosity of the photocurable resin composition, specifically, a value measured by the method described in the Examples is employed. Meanwhile, the viscosity of the composition can be adjusted by appropriately selecting the material types and contents of the components (A) to (C).

[Cured Product and Method for Producing Cured Product]

Another embodiment of the present invention is a cured product formed by curing the photocurable resin composition described above (cured product of photocurable resin composition). Here, specific examples of the cured product include an overcoat used for nail color art.

The method for producing a cured product of the photocurable resin composition (for example, an overcoat or the like) is not particularly limited, and any known method can be used. Above all, a method of curing the photocurable resin composition using energy rays is preferable. That is, the present invention also provides a method for producing a cured product by curing the photocurable resin composition with energy rays.

The method for producing a cured product is not particularly limited and any known method can be used. As an example, a method of applying the photocurable resin composition according to the present invention on a nail (fingernail) or on an artificial nail (nail tip) that has been formed in advance, and then curing the photocurable resin composition by irradiating the composition with energy rays (light or the like), may be mentioned. Furthermore, as another example, a method of molding the photocurable resin composition according to the present invention into a desired shape, and then curing the photocurable resin composition by irradiating the composition with energy rays (light or the like) is also acceptable.

The energy ray irradiation apparatus to be used at the time of curing is not particularly limited; however, a UV lamp, an LED lamp, and the like, which are commercially available, can be used. The time for irradiation with energy rays is not particularly limited; however, in the case of using an LED lamp, the time for irradiation with energy rays is preferably 5 to 120 seconds, and more preferably 10 to 30 seconds. Furthermore, in the case of using a UV lamp, the time is preferably 15 to 120 seconds, more preferably 20 to 100 seconds, and particularly preferably 20 to 70 seconds. Furthermore, the accumulated light amount is preferably 5 to 60 kJ/m$^2$. Meanwhile, upon curing, if necessary, several times of irradiation with energy rays may be carried out.

[Method for Coating (Decorating) Nail or Artificial Nail]

Another embodiment of the present invention is a method for coating a nail or an artificial nail, which includes applying the photocurable resin composition described above on a nail or an artificial nail to form a coating film, and then irradiating the coating film with energy rays to cure the coating film. Meanwhile, in the present specification, the phrase "applied on a nail or an artificial nail" includes a form of directly applying on the surface of a human nail (fingernail) or an artificial nail (nail tip), and a form of applying on the outermost surface of a single other layer or a plurality of other layers formed on the surface of a human nail or an artificial nail.

That is, a preferred embodiment of the present invention is a method for coating a nail or an artificial nail, including applying a photocurable resin composition for a nail or an artificial nail, which includes the following components (A) to (C) on a nail (fingernail) or an artificial nail to form a coating film, and then irradiating the coating film with energy rays to cure the coating film:

component (A): a compound having a (meth)acryloyl group;

component (B): a photoinitiator; and component (C): (meth)acrylic polymer particles having an average particle size of 3 to 21 μm.

The method of applying the photocurable resin composition or the method for curing a coating film (applied photocurable resin composition) is not particularly limited, and can be carried out by any technique known to those ordinarily skilled in the art. A preferred example of the method for coating a nail or an artificial nail according to the present invention will be disclosed below; however, the method according to the present invention is not limited to this method. In a case in which the photocurable resin composition of the present invention is applied directly on a nail, in order to increase the adhesiveness of a coating film, if necessary, it is preferable to perform the following operation. That is, before the photocurable resin composition is applied, it is preferable to perform sanding of the surface of a nail with a file (rasp) or the like. Subsequently, it is preferable to eliminate dust, grease, moisture, and the like with a solvent for exclusive use for a nail, which includes ethanol as a main component. Next, the photocurable resin composition of the present invention is applied on a nail or on an artificial nail with a brush, a paintbrush, or the like, so as to form a coating film having a thickness of 100 to 300 μm in a state before curing. Furthermore, the photocurable resin composition may be applied on another layer that has been formed in advance (a base coat or a cured film of a color UV nail gel). Meanwhile, a primer may be used in advance at the time of application. After the photocurable resin composition is applied to form a coating film as described above, the coating film is irradiated with energy rays, and the coating film (photocurable resin composition thus applied) is cured. The irradiation apparatus at the time of curing is not particularly limited; however, a UV lamp, an LED lamp, and the like, which are commercially available, can be used. The time for irradiation with energy rays is not particularly limited; however, in the case of using an LED lamp, the time for irradiation with energy rays is preferably 5 to 120 seconds, and more preferably 10 to 30 seconds.

Furthermore, in the case of using a UV lamp, the time is preferably 15 seconds to 120 seconds, and more preferably 20 to 100 seconds, and when the influence on the finger is considered, the time is particularly preferably 20 to 70 seconds. Furthermore, the accumulated light amount is preferably 5 to 60 kJ/m$^2$. Meanwhile, upon curing, if necessary, several times of irradiation with energy rays may be carried out. Meanwhile, upon curing, if necessary, several times of irradiation with energy rays may be carried out.

EXAMPLES

The present invention will be described in more detail below by way of Examples; however, the scope of the present invention is not intended to be limited to these Examples. Meanwhile, in the following Examples, unless particularly stated otherwise, the operation was carried out at room temperature (25° C.). Furthermore, unless particularly stated otherwise, "%" and "parts" mean "mass %" and "parts by mass", respectively.

<Production of Photocurable Resin Composition>

The following respective components were weighed at the proportions (unit: parts by mass) indicated in Table 1, and in an environment at 25° C. and under light-shielded conditions, the components were mixed for 60 minutes using a planetary mixer. Thus, a photocurable resin composition was produced.

<Component (A)> a1: Urethane acrylate oligomer (RUA-075, manufactured by Asia Industry Co., Ltd., weight average molecular weight 4,600, viscosity at 25° C. 30 Pa·s)

a2: Isobornyl acrylate (IBXA, manufactured by Osaka Organic Chemical Industry, Ltd., viscosity at 25° C. 7.7 mPa·s)

<Component (B)> b1: 1-Hydroxycyclohexyl phenyl ketone (Suncure 84, manufactured by Chemark Chemical B.V.)

b2: 2,4,6-Trimethylbenzoyl-diphenyl-phosphine oxide (SPEEDCURE TPO, manufactured by LAMBSON, Ltd.)

<Component (C)> c1: Spherical polymethylmethacrylate particles (ART PEARL GR-600, average particle size 10 μm, manufactured by Negami Chemical Industrial Co., Ltd.)

c2: Spherical polymethylmethacrylate particles (ART PEARL GR-400, average particle size 15 μm, manufactured by Negami Chemical Industrial Co., Ltd.)

c3: Spherical polymethylmethacrylate particles (ART PEARL GR-800, average particle size 6 μm, manufactured by Negami Chemical Industrial Co., Ltd.)

c4: Spherical polymethylmethacrylate particles (ART PEARL J-6PF, average particle size 4 μm, manufactured by Negami Chemical Industrial Co., Ltd.)

<Comparative Examples of Component (C)> c'1: Spherical polymethylmethacrylate particles (ART PEARL GR-300, average particle size 22 μm, manufactured by Negami Chemical Industrial Co., Ltd.)

c'2: Spherical polymethylmethacrylate particles (ART PEARL J-4PY, average particle size 2.2 μm, manufactured by Negami Chemical Industrial Co., Ltd.)

c'3: Spherical polyurethane particles (ART PEARL C-300, average particle size 22 μm, manufactured by Negami Chemical Industrial Co., Ltd.)

c'4: Spherical polyurethane particles (ART PEARL C-600, average particle size 10 μm, manufactured by Negami Chemical Industrial Co., Ltd.)

c'5: Precipitated silica (ACEMATT 3600, average particle size 5 μm, manufactured by Evonik Degussa Japan Co., Ltd.)

c'6: Fumed silica (Alu C805, average particle size 13 nm, manufactured by Evonik Degussa Japan Co., Ltd.)

c'7: Fumed silica (RM-50, average particle size 40 nm, manufactured by Evonik Degussa Japan Co., Ltd.)

c'8: Fumed silica (TT-600, average particle size 40 nm, manufactured by Evonik Degussa Japan Co., Ltd.)

c'9: Fumed silica (#200, average particle size 12 nm, manufactured by Evonik Degussa Japan Co., Ltd.)

c'10: Sillitin (AKTISIL MAM, average particle size 3.5 μm, manufactured by Tesco Co., Ltd.)

c'11: Sillitin (AKTISIL VM56, average particle size 1.5 μm, manufactured by Tesco Co., Ltd.)

c'12: Sillitin (SILLITIN Z86, average particle size 1.5 μm, manufactured by Tesco Co., Ltd.)

c'13: Sillitin (SILFIT Z91, average particle size 2 μm, manufactured by Tesco Co., Ltd.)

c'14: Talc (TALC CS, average particle size 7 μm, manufactured by Maruo Calcium Co., Ltd.)

Testing methods for the evaluations carried out for Examples and Comparative Examples of Table 1 are as follows.

<Checking of Transparency>

Into a screwed bottle (thickness 1.3 mm) made of transparent glass, each of the photocurable resin compositions according to Examples and Comparative Examples was poured to a liquid depth of 20 mm. The letters of "ThreeBond" printed in black using MS Gothic font (full-pitch characters) with a font size of 10 were placed beneath the glass bottle (screwed bottle), and transparency of the photocurable resin composition was checked by visual inspection from immediately above. The results are shown as "Transparency" in the following Table 1. In the present evaluation, in order to prevent the tinge, such as color, of another cured film (for example, a color nail) from being impaired, it is preferable that the letters are seen across the photocurable resin composition ("○" based on the following evaluation).

(Evaluation Criteria)

○: The letters of "ThreeBond" are recognizable.

×: The letters of "Threebond" are not recognizable.

<Checking of Workability>

Each of the photocurable resin compositions according to Examples and Comparative Examples was collected in an amount of 0.5 mL and was discharged into a cup for measurement. Under the following measurement conditions, viscosity measurement was carried out with an EHD type viscometer (manufactured by Toki Sangyo Co., Ltd.). In consideration of the ease of handling at the time of performing nail art, the viscosity of the photocurable resin was judged as workability. The results are shown as "Workability (Pa·s)" in the following Table 1. At the time of coating (decoration) of a nail, from the viewpoint of workability such as suppression of flow of the photocurable resin composition or ease of application, when the viscosity of the composition is less than 50 Pa·s, it is considered to be practically useful; and when the viscosity is 50 Pa·s or more, it is considered practically not useful. Furthermore, when the viscosity of the composition is less than 50 Pa·s, the composition is likely to be applied uniformly when applied on a nail using a paintbrush or the like. Meanwhile, in Table 1, the term "Unmeasurable" implies that the measurement under the following measurement conditions is beyond the limit.

(Measurement Conditions)
Cone rotor: 3°×R14
Speed of rotation: 10 rpm
Measurement time: 5 minutes
Measurement temperature: 25° C. (temperature was controlled by a constant temperature tank)

<Checking of Matte Coat (Glossiness)>

Each of the photocurable resin composition according to Examples and Comparative Examples was applied on an artificial nail (synthetic resin) with a paintbrush such that the thickness in an uncured state would be approximately 300 μm. Subsequently, a UV lamp for nails (rated voltage: 100 to 110 V, 50 to –60 Hz, power consumption: 36 W, wavelength: 350 to 400 nm) was radiated for 60 seconds, and the photocurable resin composition was cured. Uncured parts were wiped using isopropyl alcohol (IPA) soaked into waste cloth. Furthermore, an LED lamp for nails (rated voltage: 240 V, 50 to 60 Hz, power consumption: 30 W, wavelength: 400 to 410 nm) was similarly radiated for 10 seconds, and the photocurable resin composition was cured. Uncured parts were wiped using IPA soaked into waste cloth. Furthermore, a cured product was irradiated with an LED light (power consumption: 6 W), and a matte coat (glossiness of cured product) was visually recognized and judged by visual inspection according to the following evaluation criteria. The results are shown as "Matte coat" in the following Table 1. In order to obtain sufficient matte characteristics (low glossiness), according to the following evaluation criteria, it is preferable when the matte coat is "○" or "Δ", and it is particularly preferable when the matte coat is "○".

(Evaluation Criteria)

○: A uniform cured film can be formed without depending on the type of the lamp, the light of the lamp projected on the cured product is blurred on all faces, and the contour of light is not clearly seen.

Δ: a uniform cured film can be formed without depending on the type of the lamp, and the light of the lamp projected on the cured product is blurred on some faces.

×: a uniform cured film cannot be formed without depending on the type of the lamp, or the light of the lamp projected on the cured product is not at all blurred, and the contour of light is clearly seen.

TABLE 1

| Raw material | Example 1 | Example 2 | Example 3 | Example 4 | Comparative Example 1 | Example 5 | Example 6 | Example 7 | Comparative Example 2 |
|---|---|---|---|---|---|---|---|---|---|
| a1 | 60 | 60 | 60 | 60 | 60 | 60 | 60 | 60 | 60 |
| a2 | 40 | 40 | 40 | 40 | 40 | 40 | 40 | 40 | 40 |
| b1 | 6 | 6 | 6 | 6 | 6 | 6 | 6 | 6 | 6 |
| b2 | 6 | 6 | 6 | 6 | 6 | 6 | 6 | 6 | 6 |
| c1 | 126 | 50 | 110 | 150 | | | | | |
| c'1 | | | | | 126 | | | | |
| c2 | | | | | | 126 | | | |
| c3 | | | | | | | 126 | | |
| c4 | | | | | | | | 126 | |
| c'2 | | | | | | | | | 126 |
| Total | 238 | 162 | 222 | 262 | 238 | 238 | 238 | 238 | 238 |
| Transparency | ○ | ○ | ○ | ○ | ○ | ○ | ○ | ○ | ○ |
| Workability (Pa·s) | 28 | 34 | 20 | 45 | 27 | 31 | 32 | 31 | 34 |
| Matte coat | ○ | Δ | ○ | ○ | × | Δ | ○ | Δ | × |

| Raw material | Comparative Example 3 | Comparative Example 4 | Comparative Example 5 | Comparative Example 6 | Comparative Example 7 | Comparative Example 8 | Comparative Example 9 |
|---|---|---|---|---|---|---|---|
| a1 | 60 | 60 | 60 | 60 | 60 | 60 | 60 |
| a2 | 40 | 40 | 40 | 40 | 40 | 40 | 40 |
| b1 | 6 | 6 | 6 | 6 | 6 | 6 | 6 |
| b2 | 6 | 6 | 6 | 6 | 6 | 6 | 6 |
| c'3 | | 126 | | | | | |
| c'4 | | | 126 | | | | |
| c'5 | | | | 10 | 20 | | |
| c'6 | | | | | | | |
| c'7 | | | | | | 10 | |
| c'8 | | | | | | | 10 |
| c'9 | | | | | | | |
| c'10 | | | | | | | |
| c'11 | | | | | | | |
| c'12 | | | | | | | |
| c'13 | | | | | | | |
| c'14 | | | | | | | |
| Total | 112 | 238 | 238 | 122 | 132 | 122 | 122 |
| Transparency | ○ | × | × | × | × | × | × |
| Workability (Pa·s) | 1.4 | Unmeasurable | Unmeasurable | 2.1 | 3.5 | 3.4 | 5.2 |
| Matte coat | × | × | × | × | × | × | × |

| Raw material | Comparative Example 10 | Comparative Example 11 | Comparative Example 12 | Comparative Example 13 | Comparative Example 14 | Comparative Example 15 | Comparative Example 16 |
|---|---|---|---|---|---|---|---|
| a1 | 60 | 60 | 60 | 60 | 60 | 60 | 60 |
| a2 | 40 | 40 | 40 | 40 | 40 | 40 | 40 |
| b1 | 6 | 6 | 6 | 6 | 6 | 6 | 6 |
| b2 | 6 | 6 | 6 | 6 | 6 | 6 | 6 |

TABLE 1-continued

|  |  |  |  |  |  |  |  |
|---|---|---|---|---|---|---|---|
| c'3 |  |  |  |  |  |  |  |
| c'4 |  |  |  |  |  |  |  |
| c'5 |  |  |  |  |  |  |  |
| c'6 |  |  |  |  |  |  |  |
| c'7 |  |  |  |  |  |  |  |
| c'8 |  |  |  |  |  |  |  |
| c'9 | 10 |  |  |  |  |  |  |
| c'10 |  | 7 | 20 |  |  |  |  |
| c'11 |  | 3 |  | 20 |  |  |  |
| c'12 |  | 3 |  |  | 20 |  |  |
| c'13 |  |  |  |  |  | 20 |  |
| c'14 |  |  |  |  |  |  | 20 |
| Total | 122 | 125 | 132 | 132 | 132 | 132 | 132 |
| Transparency | X | X | X | X | X | X | X |
| Workability (Pa · s) | 180 | 1.6 | 1.5 | 1.6 | 1.4 | 1.7 | 1.4 |
| Matte coat | X | X | X | X | X | X | X |

It is understood that the photocurable resin composition according to Examples of Table 1 are photocurable resin compositions that have excellent transparency and workability and are capable of forming a matte coat. Meanwhile, in Examples 2, 5, and 7, the light of a lamp was generally blurred on the cured product; however, some sites where light is not blurred could be seen.

It was confirmed that since c'1 used as a filler in Comparative Example 1 had an average particle size exceeding 21 μm (average particle size=22 μm), maldistribution of the filler at the time of application was made possible, and a cured film of a uniform matte coat could not be formed. Furthermore, it was confirmed that since c'2 used as a filler in Comparative Example 2 had an average particle size below 3 μm (2.2 μm), there is luster (gloss) at the surface of the cured film, and a matte coat could not be formed. In contrast, in c1 to c4 used as fillers in Examples 1 and 5 to 7, since the average particle size was in the range of the present invention (in the range of 3 to 21 nm), sufficient matte characteristics (low glossiness) could be obtained.

Furthermore, in Comparative Example 3, since a filler was not added (not including component (C)), a matte coat could not be formed (a highly gloss cured product was obtained). In Comparative Examples 4 and 5, spherical polyurethane particles were used instead of component (C); however, it was found that compatibility with the base resin was poor and the viscosity was increased, so that workability was deteriorated. In Comparative Examples 6 to 16, fillers that are not equivalent to component (C) of the present invention were added; however, even with small amounts of fillers, the resin compositions became white and cloudy before exhibiting a matte coat, and resulted in losing transparency.

INDUSTRIAL APPLICABILITY

Since the photocurable resin composition of the present invention is a photocurable resin composition for a nail or an artificial nail that has excellent transparency and workability and is capable of forming a matte coat, the photocurable resin composition can be widely used in the field of nail care (nail art). Particularly, since the photocurable resin composition according to the present invention is excellent in transparency and a delustering effect, the photocurable resin composition is also useful as an overcoat for providing a matte texture. Furthermore, by means of the photocurable resin composition according to the present invention, effects similar to those described above can be obtained even in a case in which the photocurable resin composition is cured with a light source having a long wavelength such as 400 nm. Therefore, the photocurable resin composition according to the present invention is suitably used as a UV nail gel capable of forming a matte coat.

The present patent application is based on Japanese Patent Application No. 2016-245293, filed on Dec. 19, 2016, the disclosure of which is incorporated entirely by reference.

The invention claimed is:

1. A photocurable resin composition for a nail or an artificial nail, comprising:
    component (A): a compound having a (meth)acryloyl group;
    component (B): a photoinitiator; and
    component (C): (meth)acrylic polymer particles having an average particle size of 3 to 21 μm, and
    wherein the component (B) is contained in an amount of 8 to 25 parts by mass with respect to 100 parts by mass of the component (A), and
    the component (C) is contained in an amount of 45 to 155 parts by mass with respect to 100 parts by mass of the component (A), and
    wherein the component (B) comprises a visible light type photoinitiator and a non-visible light type photoinitiator, and
    the visible light type photoinitiator is contained in an amount of 70% by mass or less with respect to the total amount of the component (B).

2. The photocurable resin composition for a nail or an artificial nail according to claim 1, wherein the average particle size of the (meth)acrylic polymer particles of the component (C) is 5 to 14 μm.

3. The photocurable resin composition for a nail or an artificial nail according to claim 1, wherein component (A) comprises a (meth)acrylate oligomer and/or a (meth)acrylate monomer.

4. The photocurable resin composition for a nail or an artificial nail according to claim 1, wherein component (A) comprises a urethane (meth)acrylate oligomer.

5. The photocurable resin composition for a nail or an artificial nail according to claim 1, wherein component (C) is polymethylmethacrylate particles.

6. A cured product of the photocurable resin composition for a nail or an artificial nail set forth in claim 1.

7. The photocurable resin composition for a nail or an artificial nail according to claim 1, wherein the component (A) has a viscosity at 25° C. measured using an EHD type rotary viscometer of 1 mPa·s or more and 50 Pa·s or less.

8. The photocurable resin composition for a nail or an artificial nail according to claim 1, wherein the component (A) comprises a (meth)acrylate oligomer having a weight average molecular weight of 1,000 to 100,000.

9. The photocurable resin composition for a nail or an artificial nail according to claim 1, wherein a weight average molecular weight of the (meth)acrylic polymer of the component (C) is more than 100,000 and less than or equal to 11,000,000.

10. The photocurable resin composition for a nail or an artificial nail according to claim 1, wherein the photocurable resin composition has a viscosity at 25° C. measured using an EHD type rotary viscometer of 3 Pa·s or more and 50 Pa·s or less.

11. A method for coating a nail or an artificial nail, comprising applying the photocurable resin composition for a nail or an artificial nail set forth in claim 1 on a nail or an artificial nail to form a coating film, and then irradiating the coating film with energy rays to cure the coating film.

* * * * *